(12) United States Patent
Mishelevich et al.

(10) Patent No.: US 8,265,910 B2
(45) Date of Patent: Sep. 11, 2012

(54) DISPLAY OF MODELED MAGNETIC FIELDS

(75) Inventors: David J. Mishelevich, Playa del Rey, CA (US); M. Bret Schneider, Portola Valley, CA (US)

(73) Assignee: Cervel Neurotech, Inc., Foster City, CA (US)

( * ) Notice: Subject to any disclaimer, the term of this patent is extended or adjusted under 35 U.S.C. 154(b) by 0 days.

(21) Appl. No.: 12/679,960

(22) PCT Filed: Oct. 9, 2008

(86) PCT No.: PCT/US2008/079378
§ 371 (c)(1),
(2), (4) Date: Sep. 15, 2010

(87) PCT Pub. No.: WO2009/049068
PCT Pub. Date: Apr. 16, 2009

(65) Prior Publication Data
US 2011/0004450 A1    Jan. 6, 2011

Related U.S. Application Data

(60) Provisional application No. 60/978,413, filed on Oct. 9, 2007.

(51) Int. Cl.
| | |
|---|---|
| *G06F 17/50* | (2006.01) |
| *G06F 7/60* | (2006.01) |
| *G06G 7/48* | (2006.01) |
| *A61B 17/52* | (2006.01) |
| *A61B 5/04* | (2006.01) |
| *A61N 2/00* | (2006.01) |
| *A61N 1/00* | (2006.01) |

(52) U.S. Cl. ............. 703/2; 703/1; 703/3; 703/4; 703/5; 703/6; 600/9; 600/10; 600/11; 600/13; 600/14; 600/15; 600/544; 600/545

(58) Field of Classification Search ................ 703/1–6; 600/9–11, 13–15, 544, 545
See application file for complete search history.

(56) References Cited

U.S. PATENT DOCUMENTS
| | | |
|---|---|---|
| 4,134,395 A | 1/1979 | Davis |
| 4,889,526 A | 12/1989 | Rauscher et al. |
| 5,207,223 A | 5/1993 | Adler |
| 5,267,938 A | 12/1993 | Konotchick |
| 5,427,097 A | 6/1995 | Depp |

(Continued)

FOREIGN PATENT DOCUMENTS
DE    10242542 A1    4/2004

(Continued)

OTHER PUBLICATIONS

Wagner et al. "Transcranial direct current stimulation: A computer-based human model study", NeuroImage 35 (2007) 1113-1124.*

(Continued)

*Primary Examiner* — Shambhavi Patel
(74) *Attorney, Agent, or Firm* — Shay Glenn LLP

(57) ABSTRACT

Methods and systems for modeling and displaying magnetic field intensities during Transcranial Magnetic Stimulation (TMS) are described, particularly methods and system for modeling and displaying TMS using overlapping magnetic fields to stimulate deep brain regions.

11 Claims, 9 Drawing Sheets

U.S. PATENT DOCUMENTS

| | | |
|---|---|---|
| 5,441,495 A | 8/1995 | Liboff et al. |
| 5,531,227 A | 7/1996 | Schneider |
| 5,707,334 A | 1/1998 | Young |
| 5,766,124 A | 6/1998 | Polson |
| 5,891,034 A | 4/1999 | Bucholz |
| 6,042,531 A | 3/2000 | Holcomb |
| 6,132,361 A | 10/2000 | Epstein et al. |
| 6,132,631 A | 10/2000 | Nallan et al. |
| 6,179,770 B1 | 1/2001 | Mould |
| 6,179,771 B1 | 1/2001 | Mueller |
| 6,198,958 B1* | 3/2001 | Ives et al. ................ 600/411 |
| 6,236,875 B1 | 5/2001 | Bucholz et al. |
| 6,266,556 B1 | 7/2001 | Ives et al. |
| 6,351,573 B1 | 2/2002 | Schneider |
| 6,356,781 B1 | 3/2002 | Lee et al. |
| 6,425,852 B1 | 7/2002 | Epstein et al. |
| 6,447,440 B1 | 9/2002 | Markoll |
| 6,461,289 B1 | 10/2002 | Muntermann |
| 6,488,617 B1 | 12/2002 | Katz |
| 6,537,197 B1 | 3/2003 | Ruohonen et al. |
| 6,571,123 B2 | 5/2003 | Ives et al. |
| 6,572,528 B2 | 6/2003 | Rohan et al. |
| 6,663,556 B2 | 12/2003 | Barker |
| 6,827,681 B2* | 12/2004 | Tanner et al. ................ 600/9 |
| 6,849,040 B2 | 2/2005 | Ruohonen et al. |
| 6,972,097 B2 | 12/2005 | Yoshida et al. |
| 7,087,008 B2* | 8/2006 | Fox et al. ................ 600/13 |
| 7,088,210 B2 | 8/2006 | Day et al. |
| 7,104,947 B2 | 9/2006 | Riehl |
| 7,153,256 B2* | 12/2006 | Riehl et al. ................ 600/13 |
| 7,236,830 B2 | 6/2007 | Gliner |
| 7,239,910 B2* | 7/2007 | Tanner ................ 600/544 |
| 7,320,664 B2* | 1/2008 | Riehl et al. ................ 600/13 |
| 7,367,936 B2 | 5/2008 | Myers et al. |
| 7,396,326 B2 | 7/2008 | Ghiron et al. |
| 7,407,478 B2* | 8/2008 | Zangen et al. ................ 600/13 |
| 7,483,747 B2* | 1/2009 | Gliner et al. ................ 607/45 |
| 7,520,848 B2* | 4/2009 | Schneider et al. ........... 600/13 |
| 7,771,341 B2* | 8/2010 | Rogers ................ 600/9 |
| 7,856,264 B2* | 12/2010 | Firlik et al. ................ 607/3 |
| 7,904,134 B2* | 3/2011 | McIntyre et al. ............ 600/407 |
| 2002/0097125 A1 | 7/2002 | Davey |
| 2003/0004392 A1* | 1/2003 | Tanner et al. ................ 600/9 |
| 2003/0028072 A1 | 2/2003 | Fischell et al. |
| 2003/0065243 A1* | 4/2003 | Tanner ................ 600/9 |
| 2003/0204135 A1 | 10/2003 | Bystritsky |
| 2004/0010177 A1 | 1/2004 | Rohan et al. |
| 2004/0077921 A1 | 4/2004 | Becker et al. |
| 2004/0078056 A1 | 4/2004 | Zangen et al. |
| 2004/0193000 A1 | 9/2004 | Riehl |
| 2004/0193002 A1 | 9/2004 | Tanner et al. |
| 2005/0033154 A1* | 2/2005 | deCharms ................ 600/410 |
| 2005/0107655 A1 | 5/2005 | Holzner |
| 2005/0113630 A1* | 5/2005 | Fox et al. ................ 600/13 |
| 2005/0124848 A1* | 6/2005 | Holzner ................ 600/9 |
| 2005/0148808 A1 | 7/2005 | Cameron et al. |
| 2005/0154426 A1* | 7/2005 | Boveja et al. ................ 607/45 |
| 2005/0222625 A1 | 10/2005 | Laniado et al. |
| 2005/0234286 A1 | 10/2005 | Riehl et al. |
| 2005/0256539 A1* | 11/2005 | George et al. ................ 607/2 |
| 2006/0058853 A1 | 3/2006 | Bentwich |
| 2006/0094924 A1 | 5/2006 | Riehl et al. |
| 2006/0106430 A1* | 5/2006 | Fowler et al. ................ 607/45 |
| 2006/0122454 A1 | 6/2006 | Riehl et al. |
| 2006/0122496 A1 | 6/2006 | George et al. |
| 2006/0149337 A1 | 7/2006 | John |
| 2006/0173274 A1 | 8/2006 | George et al. |
| 2006/0189866 A1 | 8/2006 | Thomas et al. |
| 2006/0218790 A1 | 10/2006 | Day et al. |
| 2006/0287566 A1 | 12/2006 | Zangen et al. |
| 2007/0027353 A1 | 2/2007 | Ghiron et al. |
| 2007/0027504 A1 | 2/2007 | Barrett et al. |
| 2007/0100392 A1 | 5/2007 | Maschino et al. |
| 2007/0100398 A1* | 5/2007 | Sloan ................ 607/62 |
| 2007/0260107 A1* | 11/2007 | Mishelevich et al. ........ 600/14 |
| 2007/0265489 A1 | 11/2007 | Fowler et al. |
| 2007/0293916 A1 | 12/2007 | Peterchev |
| 2008/0033297 A1 | 2/2008 | Sliwa |
| 2008/0058582 A1 | 3/2008 | Aho et al. |
| 2008/0064950 A1 | 3/2008 | Ruohonen et al. |
| 2008/0123922 A1* | 5/2008 | Gielen et al. ................ 382/131 |
| 2008/0161636 A1 | 7/2008 | Hurme et al. |
| 2008/0306326 A1 | 12/2008 | Epstein |
| 2009/0018384 A1 | 1/2009 | Boyden et al. |
| 2009/0024021 A1 | 1/2009 | George et al. |
| 2009/0099405 A1 | 4/2009 | Schneider et al. |
| 2009/0099623 A1* | 4/2009 | Bentwich ................ 607/45 |
| 2009/0112133 A1 | 4/2009 | Deisseroth et al. |
| 2009/0112277 A1 | 4/2009 | Wingeier et al. |
| 2009/0114849 A1 | 5/2009 | Schneider et al. |
| 2009/0124848 A1 | 5/2009 | Miazga |
| 2009/0156884 A1 | 6/2009 | Schneider et al. |
| 2009/0187062 A1 | 7/2009 | Saitoh |
| 2009/0189470 A1 | 7/2009 | McClellan |
| 2009/0227830 A1 | 9/2009 | Pillutla et al. |
| 2009/0234243 A1* | 9/2009 | Schneider et al. ........... 600/544 |
| 2010/0004500 A1 | 1/2010 | Gliner et al. |
| 2011/0082326 A1 | 4/2011 | Mishelevich et al. |
| 2011/0273251 A1 | 11/2011 | Mishelevich et al. |
| 2012/0016177 A1 | 1/2012 | Mishelevich et al. |

FOREIGN PATENT DOCUMENTS

| | | |
|---|---|---|
| EP | 0501048 A1 | 9/1992 |
| EP | 0709115 A1 | 5/1996 |
| EP | 0788813 A1 | 8/1997 |
| EP | 1326681 B1 | 1/2007 |
| GB | 2271931 A | 5/1994 |
| GB | 2336544 A | 10/1999 |
| JP | 64-046479 | 2/1989 |
| JP | 5-237197 | 9/1993 |
| JP | 2003-205040 | 7/2003 |
| KR | 10-0457104 | 11/2004 |
| WO | WO 98/56302 A1 | 12/1998 |
| WO | WO 99/39769 A1 | 8/1999 |
| WO | WO 99/55421 A2 | 11/1999 |
| WO | WO 00/74777 A1 | 12/2000 |
| WO | WO 00/78267 A2 | 12/2000 |
| WO | WO 02/09811 A1 | 2/2002 |
| WO | WO 02/32504 A2 | 4/2002 |
| WO | WO 03/082405 A1 | 10/2003 |
| WO | WO 2004/087255 A1 | 10/2004 |
| WO | WO 2005/000153 A2 | 1/2005 |
| WO | WO 2006/124914 A2 | 11/2006 |
| WO | WO 2007/050592 A2 | 5/2007 |
| WO | WO 2007/130308 A2 | 11/2007 |

OTHER PUBLICATIONS

Yang, et al. "3D Realistic Head Model Simulation Based on Transcranial Magnetic Stimulation", Apr. 2006.*

Kamitani et al. "A model of magnetic stimulation of neocortical neurons", Neurocomputing 38}40 (2001) 697-703.*

Nadeem et al. "Computation of Electric and Magnetic Stimulation in Human Head Using the 3-D Impedance Method", IEEE Transactions on Biomedical Engineering, vol. 50, No. 7, Jul. 2003.*

Hsu, et al. "Analysis of Efficiency of Magenetic Stimulation", IEEE Transactions on Biomedical Engineering, vol. 50, No. 11, Nov. 2003.*

Miranda et al. "The Electric Field Induced in the Brain by Magnetic Stimulation: A 3-D Finite-Element Analysis of the Effect of Tissue Heterogeneity and Anisotropy", IEEE Transactions on Biomedical Engineering, vol. 50, No. 9, Sep. 2003.*

Schneider et al.; U.S. Appl. No. 12/838,299 entitled "Transcranial magnetic stimulation field shaping," filed Jul. 16, 2010.

Schneider et al.; U.S. Appl. No. 12/912,650 entitled "Sub-motor-threshold stimulation of deep brain targets using transcranial magnetic stimulation," filed Oct. 26, 2010.

Agnew et al.; Considerations for safety in the use of extracranial stimulation for motor evoked potentials; Neurosurgery; vol. 20; pp. 143-147; 1987.

Avery et al.; A Controlled Study of Repetitive Transcranial Magnetic Stimulation in Medication-Resistant Major Depression; Biological Psychiatry; vol. 59; pp. 187-194; 2005.

Barker et al.; Non invasive magnetic stimulation of the human motor cortex; Lancet; vol. 1; pp. 1106-1110; 1985.

Barker, A. T.; An introduction to the basic principles of magnetic nerve stimulation; Journal of Clinical Neurophysiology; vol. 8; No. 1; pp. 26-37; 1991.

Basser et al.; Stimulation of myelinated nerve axon by electromagnetic induction; Medical & Biological Engineering and Computing.; vol. 29; pp. 261-268; 1991.

Bohning et al.; Mapping transcranial magnetic stimulation (TMS) fields in vivo with MRI; NeuroReport; vol. 8; No. 11; pp. 2535-2538; Jul. 28, 1997.

Conca et al.; Effect of chronic repetitive transcranial magnetic stimulation on regional cerebral blood flow and regional cerebral glucose uptake in drug treatment-resistant depressives. A brief report; Neuropsychobiology; vol. 45; No. 1; pp. 27-31; 2002.

Dantec magnetic stimulation product information on MagPro X100 with MagOption; http://www.danica.nl/neuro/neuro-magnetische-stimulatoren.htm; Jan. 15, 2009.

Davey et al.; Designing transcranial magnetic stimulation systems; IEEE Transactions on Magnetics; vol. 41; No. 3; pp. 1142-1148; Mar. 2005.

Davey et al.; Modeling the effects of electrical conductivity of the head on the induced electrical field in the brain during magnetic stimulation; Clinical Neurophysiology; vol. 114; pp. 2204-2209; 2004.

Davey et al.; Prediction of magnetically induced electric fields in biologic tissue; IEEE Transactions on Biomedical Engineering; vol. 38; pp. 418-422; 1991.

Davey et al.; Suppressing the surface field during transcranial magnetic stimulation; IEEE Transactions on Biomedical Engineering; vol. 53; No. 2; Feb. 2006; pp. 190-194.

DeRidder et al.; Transcranial magnetic stimulation for tinnitus: influence of tinnitus duration on stimulation parameter choice and maximal tinnitus suppression; Otol Neurotol.; vol. 26; No. 4; pp. 616-619; Jul. 2005.

Epstein et al.; Magnetic coil suppression of visual perception at an extracalcarine site; J. Clin. Neurophysiol; vol. 13; No. 3; pp. 247-252; May 1996.

George, Mark S.; Stimulating the brain; Scientific American; Sep. 2002; pp. 67-73.

Han et al.; Multichannel magnetic stimulation system design considering mutual couplings among the stimulation coils; IEEE Trans. on Biomedical Engineering; vol. 51; No. 5; pp. 812-817; May 2004.

Hemond et al.; Transcranial magnetic stimulation in neurology: What we have learned from randomized controlled studies; Neuromodulation: Technology at the Neural Interface; vol. 10; No. 4; pp. 333-344; 2007.

Hovey, C. et al.; The new guide to magnetic stimulation; The Magstim Company Ltd.; Carmarthenshire, United Kingdom; 2003.

Huang et al.; Theta Burst Stimulation of the Human Motor Cortex; Neuron; vol. 45; pp. 201-206; 2005.

Isenberg et al.; Low frequency rTMS stimulation of the right frontal cortex is as effective as high frequency rTMS stimulation of the left frontal cortex for antidepressant-free, treatment-resistant depressed patients; Ann Clin Psychiatry; vol. 17; No. 3; pp. 153-159; Jul.-Sep. 2005.

Lang et al.; How does transcranial DC stimulation of the primary motor cortex alter regional neuronal activity in the human brain?; Eur. J. Neurosci.; vol. 22; No. 2; pp. 495-504; Jul. 2005.

Lin et al.; Magnetic coil design considerations for functional magnetic stimulation; IEEE Trans. On Biomedical Eng.; vol. 47; No. 5; pp. 600-610; May 2000.

Magstim Website: htttb://www.magstim.com/magneticstimulators/magstimacc/12494.html (printed Mar. 23, 2010).

Martin et al.; Transcranial magnetic stimulation for treating depression; Cochrane Review; 2002 (In (eds.): The Cochrane Library. Oxford: Update Software: The Cochrane Library. Oxford: Update Software.).

Mayberg et al.; Deep brain stimulation for treatment-resistant depression; Neuron; vol. 45; pp. 651-660; 2005.

Nadeem et al.; Computation of electric and magnetic stimulation in human head using the 3-D impedance method; IEEE Trans on Biomedical Eng; vol. 50; No. 7; pp. 900-907; Jul. 2003.

Ohnishi et al.; rCBF changes elicited by rTMS over DLPFC in humans; Suppl Clin Neurophysiol.; vol. 57: pp. 715-720; 2004.

Paton et al.; Vascular-brain signaling in hypertension: role of angiotensin II and nitric oxide; Curr. Hypertens Rep; vol. 9; No. 3; pp. 242-247; Jun. 2007.

Roth et al.; A coil design for transcranial magnetic stimulation of adeep brain regions; J. Clin. Neurophysiology; vol. 19; No. 4; 2002; pp. 361-370.

Ruohonen et al.; Theory of Multichannel Magnetic Stimulation: Toward Functional Neuromuscular Rehabilitation; IEEE Transactions on Biomedical Engineering; vol. 46; No. 6; pp. 646-651; Jun. 1999.

Ruohonen, J.; Transcranial magnetic stimulation: modelling and new techniques; (doctoral dissertation); Helsinki Univ. of Tech.; Dept. of Eng. Physics and Mathematics; Espoo, Finland; 1998.

Ruohonen et al.; (Chapter 2); Magnetic stimulation in clinical neurophysiology; Second Ed.; Ed. Elsevier Inc.; pp. 17-30; 2005.

Ruohonen et al.; Focusing and targeting of magnetic brain stimulation using multiple coils; Medical & Biological Engineering and Computing; vol. 35; pp. 297-301; 1998.

Sackheim, H. A.; Commentary: Magnetic stimulation therapy and ECT; Convulsive Therapy; vol. 10; No. 4; 1994; pp. 255-285.

Sekino et al.; Comparison of current distributions in electroconvulsive therapy and transcranial magnetic stimulation; J. of Applied Physics; vol. 91; No. 10; pp. 8730-8732; May 15, 2002.

Speer et al.; Opposite effects of high and low frequency rTMS on regional brain activity in depressed patients; Biol. Psychiatry; vol. 48; No. 12; pp. 1133-1141; Dec. 15, 2000.

Takano et al.; Short-term modulation of regional excitability and blood flow in human motor cortex following rapid-rate transcranial magnetic stimulation; Neuroimage; vol. 23; No. 3; pp. 849-859; Nov. 2004.

Traad, Monique; A Quantitative Positioning Device for Transcranial Magnetic Stimulation; Engineering in Medicine and Biology Society; 1990; Proceedings of the 12th Annual Int'l Conf. of the IEEE; Philadelphia, PA; p. 2246; Nov. 1-4, 1990.

Ueno et al.; Localized stimulation of neural tissues in the brain by means of a paired configuration of time-varying magnetic fields; J. Appl. Phys.; vol. 64; No. 10; pp. 5862-5864; Nov. 15, 1988.

Vayssettes-Courchay et al.; Role of the nucleus tractus solitarii and the rostral depressive area in the sympatholytic effect of 8-hydroxy-2-(di-n-propylamino)tetralin in the cat; Eur. J. Pharmacol.; vol. 242; No. 1; pp. 37-45; Sep. 21, 1993.

Wagner et al.; Three-dimensional head model simulation of transcranial magnetic stimulation; IEEE Trans. on Biomedical Engineering; vol. 51; No. 9; pp. 1586-1598; Sep. 2004.

Waki et al.; Junctional adhesion molecule-1 is upregulated in spontaneously hypertensive rats: evidence for a prohypertensive role within the brain stem; Hypertension; vol. 49; No. 6; pp. 1321-1327; Jun. 2007.

Wasserman et al.; Therapeutic application of repetitive magnetic stimulation: a review; Clinical Neurophysiology; vol. 112; pp. 1367-1377; 2001.

Wasserman, E. M.; Risk and safety of repetitive transcranial magnetic stimulation: report and suggested guidelines from the International Workshop on the Safety of Repetitive Transcranial Magnetic Stimulation, Jun. 5-7, 1996; Electro-encephalography and Clinical Neurophysiology; vol. 108; pp. 1-16; 1998.

Xiao et al.; Magnetic Nanocomposite Paste: An Ideal High-$\mu$, k and Q Nanomaterial for Embedded Inductors in High Frequency Electronic Appls.; Proceedings of the 9th World Multiconference on Systemics, Cybernetics and Informatics; Orlando, FL; Jul. 10-13, 2005.

Partsch et al.; U.S. Appl. No. 12/669,882 entitled "Device and method for treating hypertension via non-invasive neuromodulation," filed Jan. 20, 2010.

Schneider et al.; U.S. Appl. No. 12/671,260 entitled "Gantry and switches for position-based triggering of tms pulses in moving coils," filed Jan. 29, 2010.

Mishelevich et al.; U.S. Appl. No. 12/670,938 entitled "Firing patterns for deep brain transcranial magnetic stimulation," filed Jan. 27, 2010.

Schneider et al.; U.S. Appl. No. 12/701,395 entitled "Control and coordination of transcranial magnetic stimulation electromagnets for modulation of deep brain targets," filed Feb. 5, 2010.

Mishelevich et al.; U.S. Appl. No. 12/677,220 entitled "Focused magnetic fields," filed Mar. 9, 2010.

Mishelevich et al.; U.S. Appl. No. 12/680,749 entitled "Intra-session control of transcranial magnetic stimulation," filed Mar. 30, 2010.

Mishelevich et al.; U.S. Appl. No. 12/680,912 "Transcranial magnetic stimulation with protection of magnet-adjacent structures," filed Mar. 31, 2010.

Mishelevich et al.; U.S. Appl. No. 12/990,235 entitled "Transcranial magnetic stimulation by enhanced magnetic field perturbations," filed Oct. 29, 2010.

Schneider, M. Bret .; U.S. Appl. No. 13/169,967 entitled "Enhanced Spatial Summation for Deep-Brain Transcranial Magnetic Stimulation," filed Jun. 27, 2011.

Hayward et al.; The role of the anterior cingulate cortex in the counting stroop task; Exp Brain Res; vol. 154(3); pp. 355-358; Feb. 2004.

* cited by examiner

DISPLAY OF MODELED MAGNETIC FIELDS

CROSS REFERENCE TO RELATED APPLICATIONS

This application claims priority to U.S. Provisional Patent Application Ser. No. 60/978,413, filed on Oct. 9, 2007, titled "DISPLAY OF MODELED MAGNETIC FIELDS." This application is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The devices and methods described herein relate generally to modeling and display of electromagnetic fields of electromagnets used for Transcranial Magnetic Stimulation.

BACKGROUND OF THE INVENTION

Transcranial Magnetic Stimulation (TMS) delivered to targets within the brain or other parts of the nervous system has the capability of modulating neural activity. TMS may be used to treat many diseases and conditions. For example, positive outcomes for treatment of depression refractory to drug treatment have been demonstrated with rTMS (repetitive Transcranial Magnetic Stimulation, Avery et al., 2005). rTMS works indirectly by stimulating the dorsolateral prefrontal cortex superficially; this superficial stimulation is carried by nerve fibers to the deeper cingulate gyrus. The ability to reach deep targets is of particular interest, but practical deep-brain TMS requires stimulation at depth without over stimulating superficial tissues. More effective therapy of depression and treatment of a number of other conditions such as chronic pain, addiction, obesity, and obsessive compulsive disorder would be possible with focused brain stimulation at depth. Devices for providing deep brain stimulation with Transcranial Magnetic Stimulation are described in Schneider and Mishelevich, U.S. patent application Ser. No. 10/821,807 and Mishelevich and Schneider, U.S. patent application Ser. No. 11/429,504.

Both superficial (e.g., cortical) and deep brain stimulation would benefit from rapid and accurate modeling and display of Transcranial electromagnetic fields on brain regions including a target brain region. In particular, systems for modeling and displaying the cumulative effect of TMS from multiple magnets would be useful. Existing methods are typically directed at display of only single-magnet systems that are concerned only with superficial brain regions. Modeling and display of electromagnetic fields from TMS electromagnets capable of penetrating deeper brain regions poses significantly different issues.

Currently available methods for modeling converging magnetic fields (for example, Wagner et al, IEEE Trans. Biomed. Eng. 2004 September; 51(9):1586-98 and Davey et al., Clin. Neurophysiol. 2003 November; 114(11):2204-9) are computationally intensive, and employ expensive software, such that making simple estimations of physically overlapping magnetic-field strengths may not be practical. In order to facilitate rapid device design and TMS treatment planning, there is a need for improved means for displaying modeled magnetic-field intensity at depth to assess the impact of different configurations of electromagnets in space and time for research or treatment planning. This includes the shaping of the magnetic fields generated by electromagnets by influences such as other electromagnets and high-permeability magnetic regions.

Hurme et al., U.S. patent application Ser. No. 11/853,232 and International Patent Application PCT/EP2007/059589, describes a method for displaying a visualization surface representative of a portion of the brain at a given depth overlaid on a volumetric image of the brain, the TMS-coil induced electric field and the coil itself. This display only relates to superficial brain just below the cranium rather than targets at depth.

SUMMARY OF THE INVENTION

Described herein are methods and systems for the modeling and displaying the intensity of magnetic fields used for Transcranial Magnetic Stimulation (TMS), including where magnetic fields overlap in space or time. In particular systems and methods for modeling and displaying the intensity of magnetic fields when using multiple TMS coils to stimulate deep (e.g., sub-cortical) brain targets. Systems and device for planning a treatment using a plurality of TMS electromagnets are also described.

The visual models and display methods described may be particularly useful in rapidly (e.g., real time) mapping magnetic fields generated by multiple TMS electromagnets to stimulate deep brain targets. Thus, these methods and device may be adapted to calculate treatments for stimulation of deep-brain targets even when the electromagnets are moving.

In previously described methods and devices for deep-brain stimulation (see, e.g., U.S. patent application Publication Ser. Nos. 11/429,50 (titled "Trajectory-Based Transcranial Magnetic Stimulation") and 10/821,807 (titled "Robotic apparatus for targeting and producing deep, focused Transcranial Magnetic Stimulation"), stimulation of deep-brain regions involves stimulation of a single brain region from multiple sites, either by moving the electromagnet sufficiently quickly so that the effect of stimulation from different sites sums, or by stimulating the same brain region from multiple sites outside of the brain using different electromagnets. In both cases the electromagnetic field is directed to a deep brain target but must pass through intervening non-target (e.g., cortical) brain regions. The intervening non-target brain region may be the region of the brain between the deep brain target and the coil. Examples of deep brain targets may include cingulated gyrus and other brain nuclei. In some variations it may be desirable to stimulate deep brain regions above the motor threshold (100% MT), but stimulate intervening non-target regions at below MT (<100% MT).

The present system and methods allow modeling of the magnetic field (and therefore of the stimulation) of both target and non-target regions. These models and display methods may therefore be used to design a treatment. For example, by modeling and displaying the magnetic field at both a deep-brain target region and non-target regions (e.g., intervening regions), it may be possible to plan a treatment that stimulates target regions while minimizing or optimizing the effects of non-target regions.

In general, the methods and systems described herein determine and display magnetic fields by first determining the position of each of a plurality of TMS electromagnets relative to a patient's head (and/or brain) and then by spatially and/or temporally summing the components of the magnetic field at target and non-target brain regions based on the intensity of the magnetic fields, which are pre-calculated for each TMS electromagnet. The combination of linear summing and using pre-calculated magnetic field models for each TMS electromagnet allows the methods and systems described herein to quickly model and display magnetic field intensities in both target and non-target regions.

In some variations of the methods and systems described herein the magnetic field intensities at various target and non-target brain regions may be determined for one or more electromagnets as they are moved or re-oriented around a patients head and brain. Thus, in some variations the modeling may be time dependent, and the magnetic field intensity at one or more target and non-target brain regions, may be summed in time, over a window of time that reflects the movement of one or more TMS electromagnets and the duration of the effect of magnetic stimulation on the target and non-target regions. For example, one or more time constant (τ) that reflects the duration of magnetic stimulation may be used scale the effect of stimulation on the target and non-target brain regions. In other variations the systems and methods may be used in static systems in which the TMS electromagnets do not move relative to the head/brain between stimulation periods.

Pre-calculation of the magnetic field models for each of the TMS electromagnets may be performed as part of the methods described herein, or it may be performed prior to the start of any of these methods. For example, pre-calculated magnetic field models may be provided. As used herein, "pre-calculated" refers to determining a magnetic field model for a TMS electromagnet before calculating the magnetic field intensity on a target or non-target region. "Pre-calculated" magnetic field models may be calculated by mathematical methods, or by empirical methods (e.g., measuring the magnetic field intensity at various positions.

For example, described herein are methods of modeling Transcranial Magnetic Stimulation (TMS) on a deep brain target, in which the method includes the steps of: arranging representations of a plurality of TMS electromagnets around a model of a patient's head, wherein each TMS electromagnet has a pre-computed magnetic field model; calculating the intensity of the magnetic field at each of a plurality of brain regions by summing the magnetic field intensities of the portions of the pre-computed magnetic field model for each TMS electromagnet at each brain region; and displaying the calculated magnetic field intensities for each of the plurality of brain regions.

The order of the steps of any of these methods may be different, unless the context explicitly requires otherwise.

The step of arranging representations of a plurality of TMS electromagnets around a model of a patients head may include moving an electronic representation of a TMS electromagnet around an electronic (e.g., computer-generated) model of a patient's head. The model of the patient's head may be a model of just the brain, or it may include other anatomical regions (e.g., skull, skin, etc.). The model of the patient's head may be taken or derived from imaging performed on the actual patient (e.g., MRI or other brain or biological scans). Thus, in some variations the method also comprises registering the position of the representations of the TMS electromagnets relative to the model of the patient's head with the position of actual TMS electromagnets relative to the patient's head.

The step of arranging the representations may also include arranging a plurality of actual TMS electromagnets around a patients head, and registering the representation of the TMS electromagnets and/or head with a computer-generated representation of the patient's head/brain. Any appropriate registration method and system or sub-system may be used. For example, Ruohonen et al (e.g., U.S. patent application publication no. 2008/0064950) and Hurme et al. (U.S. patent application publication no. 2008/0161636) describe various registration methods for single TMS electromagnets. Registration of multiple TMS electromagnets with the patient's head may be performed by optical, magnetic, acoustic or other registration methods. In some variations each TMS electromagnet may include one or more fiduciary markers indicating the position and/or orientation of the TMS electromagnet; the patient's head may also include one or more fiduciary markers. These markers may be used to determine the relative positions (e.g., register) the TMS electromagnets and the patient's head.

In some variations, the step of pre-computing the magnetic field model for each of the TMS electromagnets may be included. In other variations the method may include the step of providing pre-computed magnetic field models for each of the TMS electromagnets.

The step of calculating may include calculating using the pre-computed magnetic field model for each TMS electromagnet wherein each pre-computed magnetic field model comprises an array of magnetic field intensities indexed by positions that are a predetermined distance from the TMS electromagnet, further wherein each position has a magnetic intensity value representing the magnetic intensity at that position. As described in greater detail below, the index of positions may be limited to range of positions relevant to the patient's head. In some variations the pre-computed magnetic field model for each TMS electromagnet has a resolution of less than about 1 mm (e.g., about 0.5 mm, about 0.25 mm, 0.1 mm, etc.). In some variations the pre-computed magnetic field model for each TMS electromagnet is also indexed by applied energy. For example, the magnetic field intensity value at a particular position may be dependent on the current applied to the TMS electromagnet. The array of field intensities may therefore be indexed by position (e.g., within a range of distances from the TMS electromagnet) and applied energy (e.g., within a range of applied energies).

The step of calculating may therefore comprise calculating using the pre-computed magnetic field model for each TMS electromagnet wherein the pre-computed magnetic fields have a resolution of less than about 1 mm. For example, the spatial resolution of the indexing distance for the array of magnetic field intensity values may be less than 1 mm (e.g., less than 1 mm "voxels" in three-dimensional space).

The step of calculating may include the steps of applying the magnetic field intensity models for each TMS electromagnets to the same coordinate system as the brain and target/non-target regions. For example, if the brain is on first coordinate system, the position and orientation of each of TMS electromagnets may be determined in this first coordinate system. The conversion between the coordinate system of an individual TMS electromagnet and the first coordinate system can be used to determine the index value used to look up the magnetic field intensity for coordinates within the target region(s) and non-target regions for that TMS electromagnet based on its pre-determined magnetic field model. The position of each coordinate in a brain region (e.g., target and non-target) in the first coordinate system may then be used to look up (from the pre-determined magnetic field model) the magnetic field intensity at that brain region for each TMS electromagnet. These intensity values may then be simply summed. In some variations the simulated power applied to each TMS electromagnet may also be used to look up the magnetic field intensity value.

In some variations, the method also includes the steps of iteratively moving and recalculating the magnetic field intensity due to the TMS electromagnets. For example, the method may include the steps of moving the representations of one or more of the TMS electromagnets relative to the model of a patient's head; re-calculating the intensity of the magnetic field for each of a plurality of brain regions; and displaying the re-calculated magnetic field intensities for each of the plurality of brain regions. Thus, the step of calculating the intensity of the magnetic field for each of a plurality of brain regions may include comprises linearly summing the overlapping magnetic field intensities for each brain region.

As mentioned, the target brain region is typically a non-cortical, e.g., deep-brain target. For example, the target may be cinguate gyms.

Also described herein are methods of generating a Transcranial Magnetic Stimulation (TMS) treatment plan for a patient, including the steps of: displaying representations of a plurality of TMS electromagnets around a model of the patient's brain; calculating the intensity of the magnetic field for a plurality brain regions including a deep brain target based on the positions of the TMS electromagnets relative to the brain and based on pre-computed magnetic field models for each of the plurality of TMS electromagnets; displaying the magnetic field intensity at the deep brain target on the model of the patient's brain and on non-target regions in the patient's brain; and moving the representation of at least one TMS electrode and re-calculating the intensity of the magnetic field for the deep brain target until the magnetic field intensity at the deep brain target is above a stimulation threshold while the magnetic field intensity at non-target regions is below a stimulation threshold.

The method may also include displaying a model of the patient's brain and determining a deep brain target on the model of the patient's brain.

As discussed above, these methods may also include pre-computing the magnetic field model for each of the TMS electromagnets, and registering the position of the representations of the TMS electromagnets relative to the model of the patient's head with the position of actual TMS electromagnets relative to the patient's head.

The step of calculating the intensity of the magnetic field for each of a plurality of brain regions may include linearly summing the overlapping magnetic field intensities for each brain region, as described.

Also described herein are systems for modeling Transcranial Magnetic Stimulation (TMS) on a deep brain target. For example, a system may include: a plurality of TMS electromagnets configured to be positionable at different locations and orientations around a patient's head; a registration subsystem configured to determine the positions and orientations of each of the plurality of TMS electromagnets and the patient's head; a magnetic field intensity modeling unit configured to calculate the intensity of the magnetic field for a plurality brain regions including a deep brain target and non-target regions based on the positions and orientations of the TMS electromagnets relative to the patient's head (and/or brain) and based on pre-computed magnetic field models for each of the plurality of TMS electromagnets; and a display unit configured to display the magnetic field intensity determined by the magnetic field intensity modeling unit.

The display unit may be configured to display the magnetic field intensity in three dimensions, or in two-dimensions, or both. In some variations the display may be configured to show the intensities over time. The display unit may include a monitor (or monitors) and control logic for controlling the display.

The system may also include a controller configured to control the position and orientation of the TMS electromagnets. In some variations, each of the plurality of TMS electromagnets are configured to move (e.g., rotate, turn in roll, pitch, yaw, etc.) relative to the patient's head. For example, the system may include a gantry or track on which the TMS electromagnets move around the patient's head. One or more drivers may move the TMS electromagnets, and the controller may coordinate the movement (and the application of power).

In some variations, the magnetic field intensity modeling unit comprises treatment planning logic configured to determine if the magnetic field intensity of the deep brain target is greater than a threshold while the magnetic field intensity at non-target regions is below a stimulation threshold. For example, the threshold be the motor threshold (MT), which may be indicated as "100% MT" (above threshold) for stimulation at those regions. "MT" refers to motor threshold, a standard (based on stimulation of motor cortex) for evoking a response via Transcranial Magnetic Stimulation; "100% MT" or greater (e.g., "115% MT") may result in an evoked action potential. The stimulation applied from individual TMS electromagnets may be below threshold (<100% MT), while still summing to provide sufficient (at or above 100% MT) for a deep brain target. It may be desirable to have non-target regions (e.g., cortical or regions superficial to the target between the target and the TMS coils) may be un-stimulated so that they do not fire action potentials, while still stimulating the deeper region(s), and therefore below MT.

DETAILED DESCRIPTION OF THE INVENTION

Figure 1:
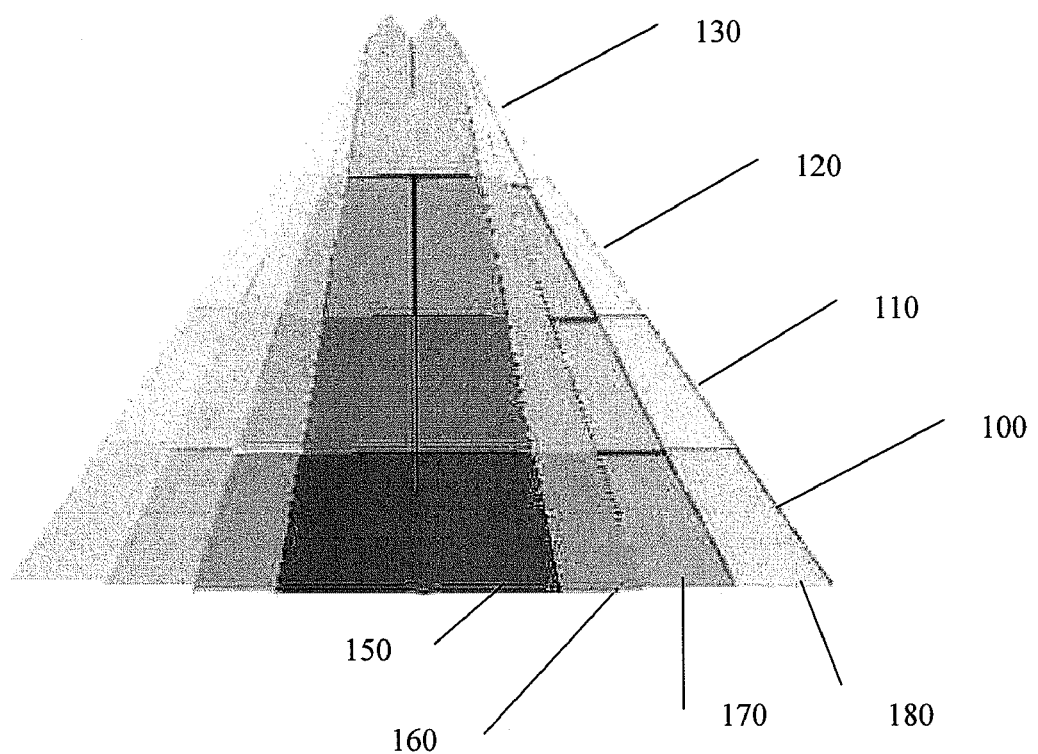
FIG. 1 shows a two-dimensional representation of a dual-gradient magnetic field profile generated from a single TMS electromagnet.

The systems and methods described herein typically determine and display magnetic fields applied by Transcranial Magnetic Stimulation (TMS) electromagnets for stimulation of a deep-brain target. In some variations, these methods and devices first determine the position of each of a plurality of TMS electromagnets relative to a patient's head (and/or brain) and then calculate the magnetic field intensity by spatially and/or temporally summing the overlapping magnetic field components of each TMS electromagnet to determine the magnetic field intensity at target and non-target brain regions. The calculation of the magnetic field intensity is done by linear summation using pre-calculated magnetic field models for each TMS electromagnet.

Each TMS electromagnet may have a unique pre-calculated magnetic field model, or similar TMS electromagnets may have identical TMS electromagnets. The pre-calculated magnetic-field models for each TMS electromagnet can be generated from theoretical models (e.g., based on the size, shape and power of the TMS electromagnet) or obtained from empirical measurements, or some combination thereof. As used herein, "pre-calculated" magnetic field models for TMS electromagnets may be pre-calculated by empirical measurement. Although the magnetic field model for a particular TMS electromagnet may be specific to the shape and configuration of the TMS electromagnet, in some variations a generic pre-calculated magnetic field model may be used for multiple TMS electromagnets. In some variations of the systems described herein, a look-up references or tables of pre-calculated magnetic field models for a variety of TMS electromagnets. The shape and size of the TMS electromagnet may be used to determine which of the pre-calculated magnetic field models to apply.

The pre-calculated magnetic field model for any particular TMS electromagnet may be an array of values, including an array of position and intensity values. For example, a particular TMS electromagnet's magnetic field model may be an n-dimensional array of magnetic field intensities indexed by position (e.g., x,y,z or z,r,θ), and may also be indexed by the energy applied to the TMS electromagnet (e.g., i). In some variations the intensity is assumed to be at a pre-determined (e.g., peak or average) applied energy, and is therefore not included in the magnetic field model. Thus the magnetic field model may be the array of magnetic field intensities over a range of positions and also applied energies. Since magnetic field intensity falls off rapidly with distance from the magnet (e.g., $1/distance^3$), the range of locations may be limited. The range may be further limited to regions which would reasonably be within the brain. For example, the array of magnetic field intensities in each model may be pre-calculated or experimentally determined only for spatial coordinates less than the diameter of the human head, and only for one hemisphere around the TMS electromagnet (e.g., the direction which will face the patient). Thus, the coordinates x,y,z or z,r,θ may be limited. In some variations only two dimensions (e.g., x,y or r,θ) are used. For example, the magnetic field intensity in only two dimensions may be determined.

A pre-calculated magnetic field model may also be divided up into a finite range of values, which may be based on position. Thus, the array of magnetic field intensities for each magnetic field model may be thought of as describing finite voxels (adjacent volumes), wherein the magnetic field intensity describes the magnetic field intensity (e.g., on average) for that volume/voxel. The size of the voxel may be increased (decreasing resolution) or decreased (increasing resolution). The higher the resolution the greater the size of the array representing the magnetic field model. In some variations the minimum voxel (volume unit) size is less than about 1 mm.

The methods described herein including primarily visual methods including the display of magnetic fields from one or more TMS electromagnet, and the display of overlapping regions. Magnetic fields may be displayed simultaneously with display of a patients head and/or brain. Various regions, including target regions, may be identified (e.g., outlines, colored, etc.) in the display. Displays may be shown in two or three spatial dimensions, or some combination of two and three-dimensional displays. In some embodiments, the displays are generated in two- or three-dimensional forms using mechanical computer-aided design systems such as Alibre Design or SolidWorks and in others by custom software.

Figure 2:
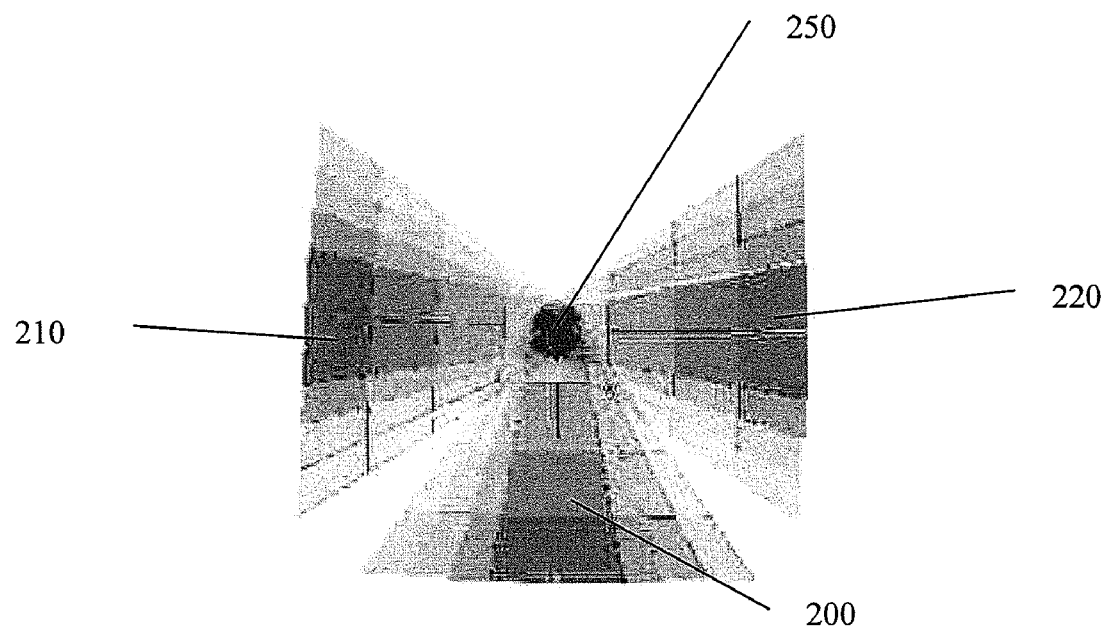
FIG. 2 is a two-dimensional display of overlapping magnetic fields with two gradient intensities based on distances both from faces of electromagnets and laterally showing overlap at the target.

An example of a two-dimensional display showing a field from a TMS electromagnet is shown in FIG. 1. FIG. 2 shows a two-dimensional display of the magnetic field intensities from three TMS electromagnets. For example, in FIG. 1, the outline shape of the display of magnetic intensity illustrates the characteristics of the electromagnet itself combined with any external influences such as other electromagnets (static or pulses fields) or high-permeability magnetic regions. Two intensity gradients are shown in FIG. 1, these gradients are shown as regions having relatively similar magnetic intensities, indicated by the shading. Each of the regions shown as part of the two-dimensional field intensity may be thought of as a unit of the magnetic field model for the TMS electromagnet. Although the size of the regions are shown increasing with distance from the TMS coil, in many of the variations described herein, the size of a spatial unit (e.g., voxel) for a magnetic field model may be uniform. The first represents the decreasing intensity as one moves outwards from the face of the electromagnet along an axis that is perpendicular to the face of the electromagnet. In FIG. 1, there are four levels of such intensities, 100, 110, 120, and 130. Shading represents magnetic field intensity so the magnetic intensity represented by band 100 that is closest to the electromagnet face is greater than that of band 110 that is further away from the face. The second gradient represents decreasing intensity as one moves laterally from the center of the electromagnet. In FIG. 1, there are four levels of such intensities, 150, 160, 170, and 180. The lateral changes shown are symmetric around the midline. Given the double gradient, with four intensities in each direction in the figure, there are 16 different values (spatial elements). It is to be understood that there may be lesser or greater resolution in one or both directions, increasing towards continuously varying intensities. Intensity changes represent the properties of the TMS magnetic field. The characteristics of the model will vary if the electromagnet is not symmetric along one or more axes.

FIG. 2 illustrates a display showing a two-dimensional representation of the magnetic-field profiles of a plurality of TMS electromagnets similar to the type shown in FIG. 1. The two-dimensional profiles 200, 210, and 220 represent three individual electromagnets or one or more electromagnets that are moved quickly enough from one position to another so the effects on the target neural structure overlap. This movement must between with a time constant of the effect of the magnetic field on the brain tissue, so that the effect of the magnetic field may sum temporally. Variations in intensity are as discussed in conjunction with FIG. 1. Any number of electromagnets (e.g., greater than two but typically at least four) will demonstrate the same effect, and can be summed in intensity as shown.

FIG. 2 illustrates a simplified display of three TMS electromagnets. In this example, the TMS electromagnets are not displayed overlapping with a region of the brain, however it should be understood that generally the display will also illustrate the patient's brain, and may indicate a target region. Each of the TMS coils whose fields are indicated in FIG. 2 have pre-calculated magnetic fields similar to those shown in FIG. 1. In this example, the magnetic field intensities of regions that do not overlap are either zero, or equal to the magnetic field intensity as determined by the TMS electromagnet. In overlapping regions (e.g., the center region 250), the magnetic field intensity is determined by linearly summing the magnetic field intensities of all three of the individual fields as applied to the same space 250. Thus, the magnetic field intensity at the position 250 is equal to the magnetic field intensity from the first TMS coil at position 250, plus the magnetic field intensity from the second TMS coil at position 250, plus the magnetic field intensity from the third TMS coil at position 250.

In FIG. 2, the intensity (seen by the darker shading) of the overlap 250 is greater than the darkest (highest intensity) bands at the periphery. Thus, the target region at the center (the overlapping region) would receive the highest combined intensity of stimulation, as compared to any other point and may therefore undesirable side effects of stimulation of superficial tissues at the periphery are avoided. This may be particularly true if the threshold for stimulation (e.g., MT) is reached at the center 250 region, but not at the edge regions. Thus, the methods and devices described herein may allow comparison of the magnetic field intensity at any point or region (e.g., the target region and surrounding non-target regions including the regions closest to the TMS coils), with one or more thresholds. The display may include an indicator of the threshold (e.g., text, color, etc.). Although the figures shown herein are in grayscale, in some variations the figures (e.g., the magnetic field intensity) is in color. Color may also be used to indicate polarity of the field, as well as the absolute intensity.

Figure 3A:
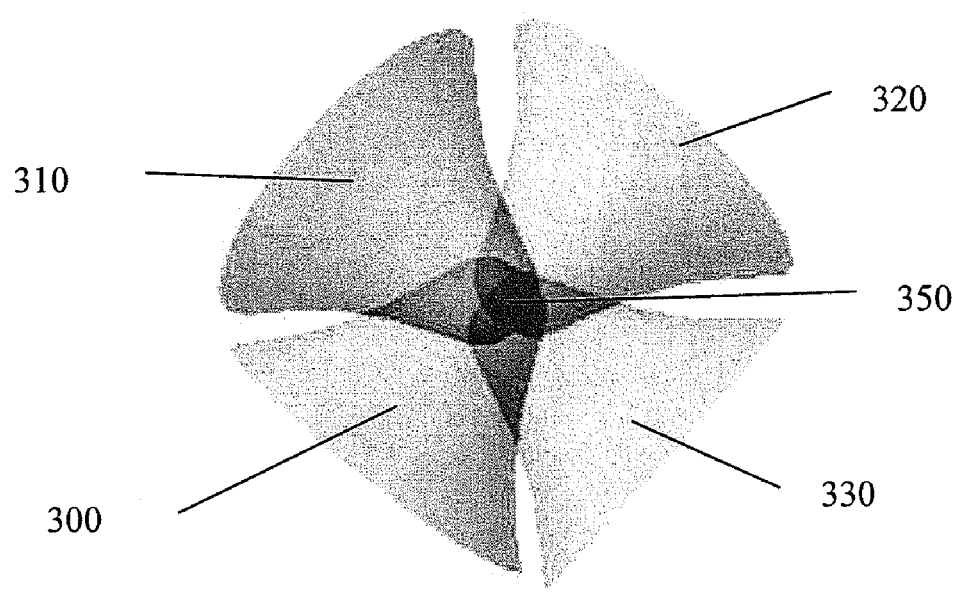
FIG. 3A is a three-dimensional display of overlapping magnetic fields at target without gradient intensities shown.
Figure 3B:
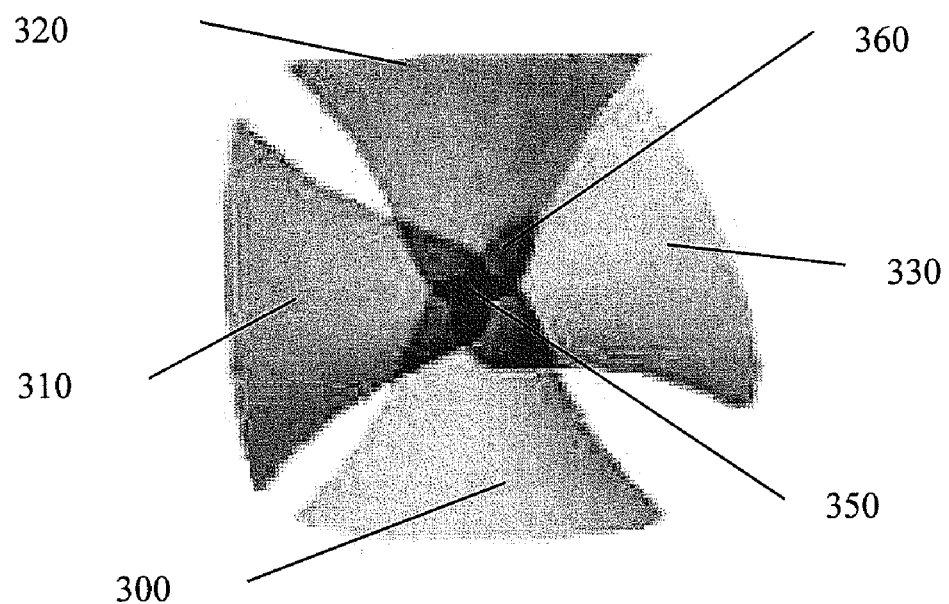
FIG. 3B is a three-dimensional display of overlapping magnetic fields at target and periphery without gradient intensities shown.
Figure 4:
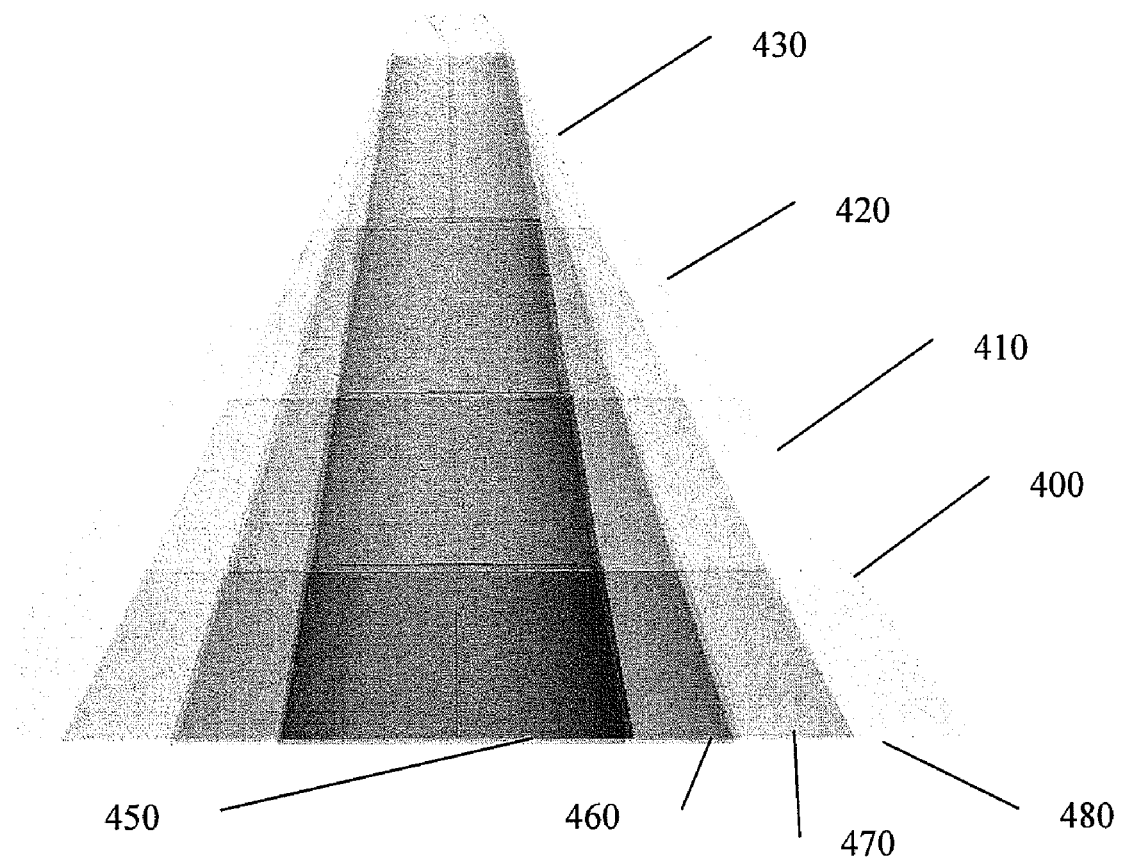
FIG. 4 is a three-dimensional representation of a dual-gradient magnetic field profile generated from a single electromagnet.
Figure 5:
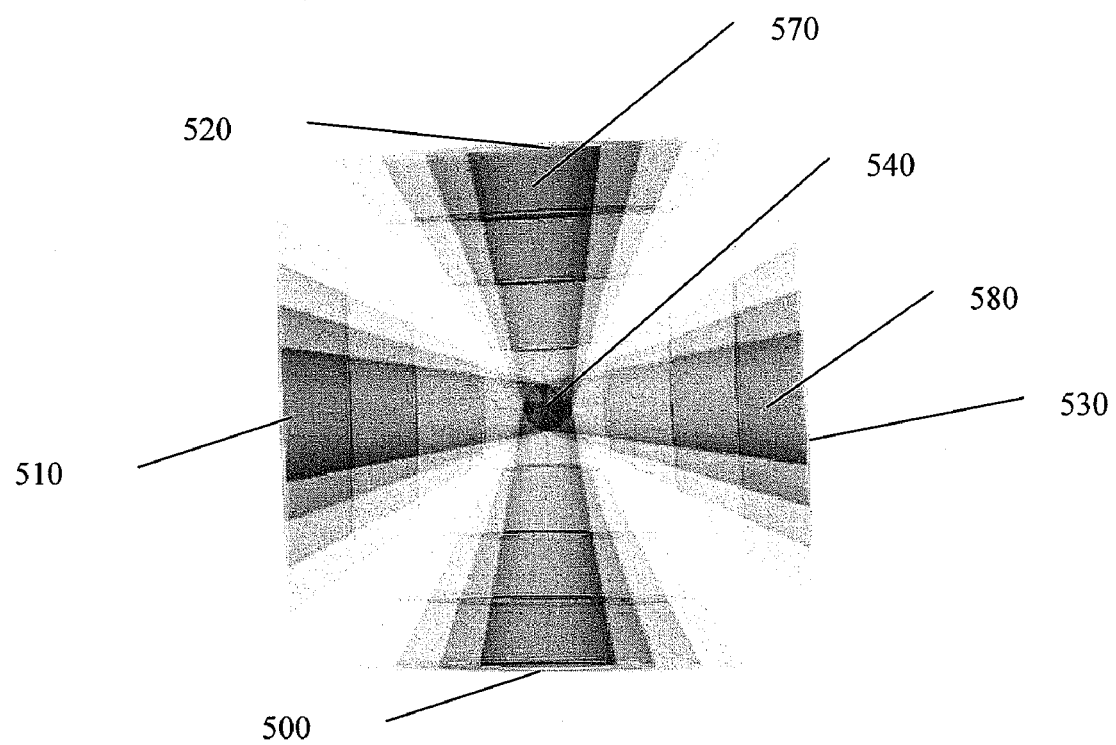
FIG. 5 is a three-dimensional display of overlapping magnetic fields with gradient intensities based on distances both from faces of electromagnets and laterally.

FIGS. 3 through 5 illustrate three-dimensional displays of magnetic field intensity that are calculated similar to the two-dimensional displays just described. The magnetic-field profiles shown are the type generated by double-coil electromagnets such as those available from Magstim, Ltd. (Wales, UK) or those generated by any other types of electromagnets commonly used for TMS. It is not always necessary to display a gradient for one or all of the electromagnets. FIGS. 3A and 3B illustrate this. For example, FIGS. 3A and 3B show bell-shaped profiles 300, 310, 320, and 330 whose central ends overlap at target 350. The increased darkness of the overlapping region demonstrates that a higher intensity is delivered to target 350. In FIG. 3A, the peripheries of the magnetic field profiles 300, 310, 320, and 330 do not overlap so there would be no significant superficial interactions in any case. The target 350 is the region of highest intensity (within predetermined field-strength-cutoff points) in FIG. 3B, even when compared to overlap 360 at the peripheries of the fields from electromagnets 320 and 330. Alternatively, there are situations in which the intensities of overlaps such as 360 represent as much or more stimulation at the periphery than at the target. This may be the case where there is an increased risk that undesirable side effects such as seizures would occur. This display may therefore demonstrate a situation to be avoided. As mentioned, the display may also indicate regions above a stimulation threshold (e.g. MT), such as this region. Not all such overlaps are problematic, only ones where the intensity at a given location would give rise to undesirable side effects.

FIGS. 4 and 5 illustrate three-dimensional magnetic field models for TMS electromagnets that also have dual intensity gradients such as described above for FIG. 1; one decreasing with increasing distance from the face of the electromagnet (intensity bands 400, 410, 420, and 430) and the second as one moves laterally (intensity bands 450, 460, 470, and 480). Again, because of four levels in the first direction and four levels in the second, there are 16 different levels in 32 regions in this example. As in the two-dimensional case, there can be lesser or greater resolution (e.g., number of spatial regions, or voxels) even down to continuous variation. The combination of such profiles is demonstrated in FIG. 5, in which profiles 500, 510, 520, and 530 overlap at target position 540.

An example of a possible complicating factor in interpretation of the display is the difference of darkness for a same given intensity because of the viewing angle of the three-dimensional display. Such a case is demonstrated by comparing the darkness of intensity band 570 in magnetic profile 520 to the darkness of intensity band 580 in magnetic profile 530. Even though the magnetic-field intensities represented by bands 570 and 580 are identical, band 570 may appear darker than band 580 due to the shading effects of the three-dimensional display. It is thus important for the user to be aware and correctly interpret the significance of the darkness in each case. Also, to compensate for such effects, one additional embodiment may include intensity gradients that continuously vary as opposed to the 16 intensity-level displays shown in FIGS. 4 and 5 and still another embodiment eliminates the intensity gradient entirely. In some variations, the intensity levels may be determined by color (as indicated) may be shown only as above/below a threshold indicators (e.g. blue when below, red when above).

The shape of the profile when viewed directly towards the electromagnet may depend on the physical configuration of the electromagnet. In FIG. 4, the profile is circular. It is to be understood that other embodiments such as oval, dumbbell, or any other shapes may also be described, depending on the magnetic field generated by the physical configuration of the given electromagnet. It is also to be understood that the face of the electromagnet need not be flat, and the methods and devices described herein could be applied by including the pre-calculated intensity-profile shape of any given electromagnet(s). Again, in any case, the fields from multiple electromagnets can be combined by linear addition once the coordinate system has been adjusted and the pre-calculated magnetic field models applied.

The intensity levels as a function of the distance of the given point away from the face of the electromagnet can be set by the user to facilitate communicating the effects and may or not reflect the theoretical fall off of magnetic-field intensity as a function of the axial distance from the electromagnet face as predicted by the Biot-Savart Law. As to the 1 over $r^3$ or $r^2$ fall-off, for TMS magnets the relationship is on the order of $1/r^2$ for axial distances that are short relative to the longest dimension of the face of the electromagnet and on the order of $1/r^3$ for distances that are long relative to the longest dimension of the fact of the electromagnet. While the intensities in the embodiments shown in the figures are shown as variations in shading, other embodiments include variations in color or variations in both shading and color.

None of the three-dimensional models describe herein assume that the central axes of the magnetic-field profiles (for example 500, 510, 520, and 530 in FIG. 5) are required to reside in the same plane. The number of electromagnets is not limited to up to four; any number of electromagnets that can physically be accommodated can be used.

Other embodiments include displays of the effects of multiple electromagnets or arrays of electromagnets whose magnetic fields overlap. Further additional embodiments incorporate animated simulations where the magnetic profiles move and overlapping of magnetic fields viewed dynamically. For example, if the rotation of one or more electromagnets on a gantry is involved (e.g., Schneider and Mishelevich, U.S. patent application Ser. No. 10/821,807), the effects of overlaps (desirable or undesirable) may be viewed as functions of both space and time. Thus, the impacts of variation of parameters such as velocity or angle can thus be effectively assessed. For example, if one or more of the electromagnets are rotated then the overlaps are presented in real-time or scaled real time so the net impact on the target and other regions can be assessed. In one variation, the NASTRAN Motion simulation or similar methods may be used in the context a three-dimensional mechanical CAD (Computer-Aided-Design) system to illustrate the overlap in pre-calculated magnetic field models applied to a model of the patient's brain.

In some embodiments, any motion (whether taken as configuration snapshots at a given point in time or animated) may be displayed. Sample motions include rotation or moving one or more electromagnets back and forth with motion in one direction timed to firing of the electromagnets to reach the target neural structures.

In predicting the effect of magnetic stimulation using any of these embodiments, it is important to account for both the position of a given electromagnet, and also whether that electromagnet is fired. If an electromagnetic is being moved (rotated around a patient's head, for example), it need not be fired each time at the same position in the orbit. Thus, in some variations the methods described herein may be repeated to determine the effect of TMS stimulation at different times.

The display of the fields my extend out a distance to an arbitrary cutoff as described here, but other included embodiments may go outward and/or laterally to any selected distance.

Figure 6:
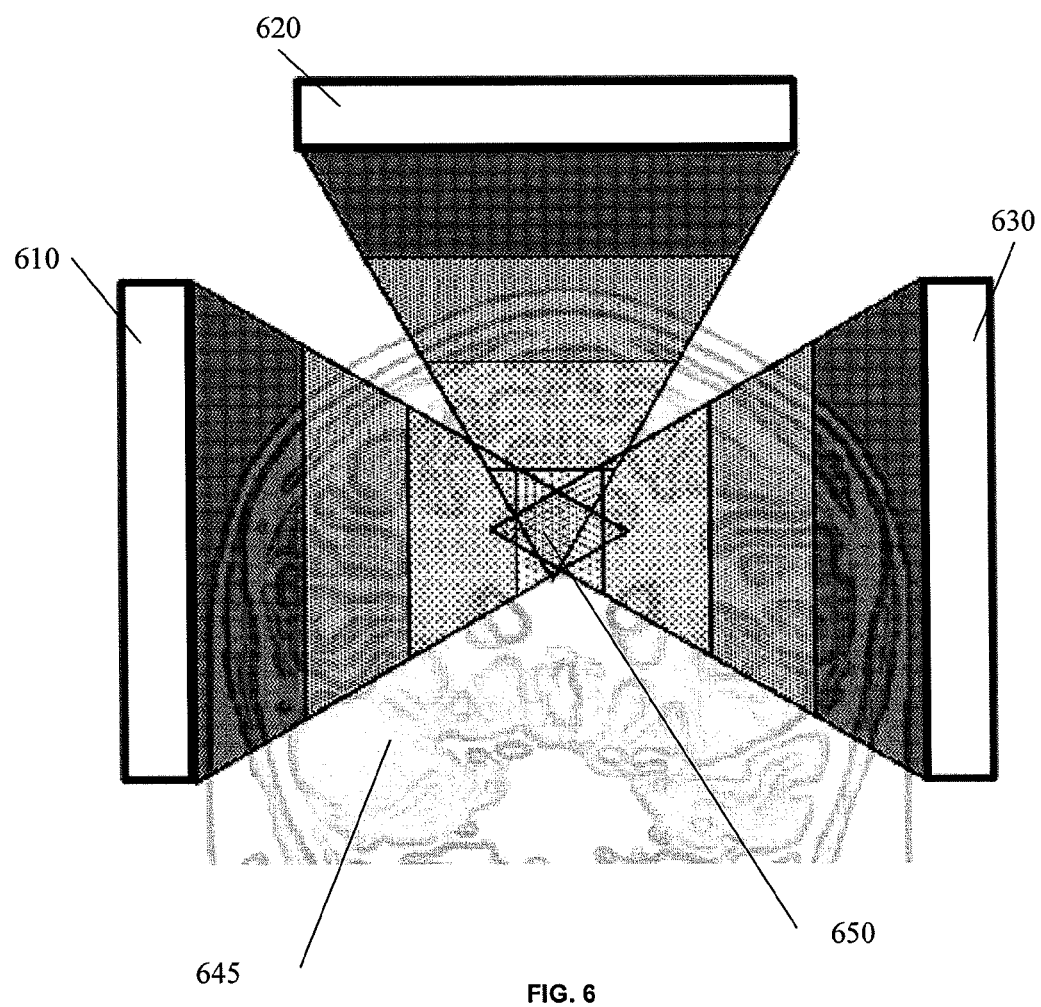
FIG. 6 illustrates one variation of a display showing a 2D cross-section through a region a brain and the magnetic field intensities from three TMS electromagnets.

As mentioned, any of the variations described herein may be illustrated in conjunction with an image of the patients head and/or brain. FIG. 6 illustrates one variation in which a two-dimensional image of the magnetic field intensity (shown here in four levels indicated by stippling) from each of three TMS coils 610, 620, 630 may be shown on top of a section through a patient's brain 645. The overlapping region 650 occurs in the deep brain region shown.

Figure 7:
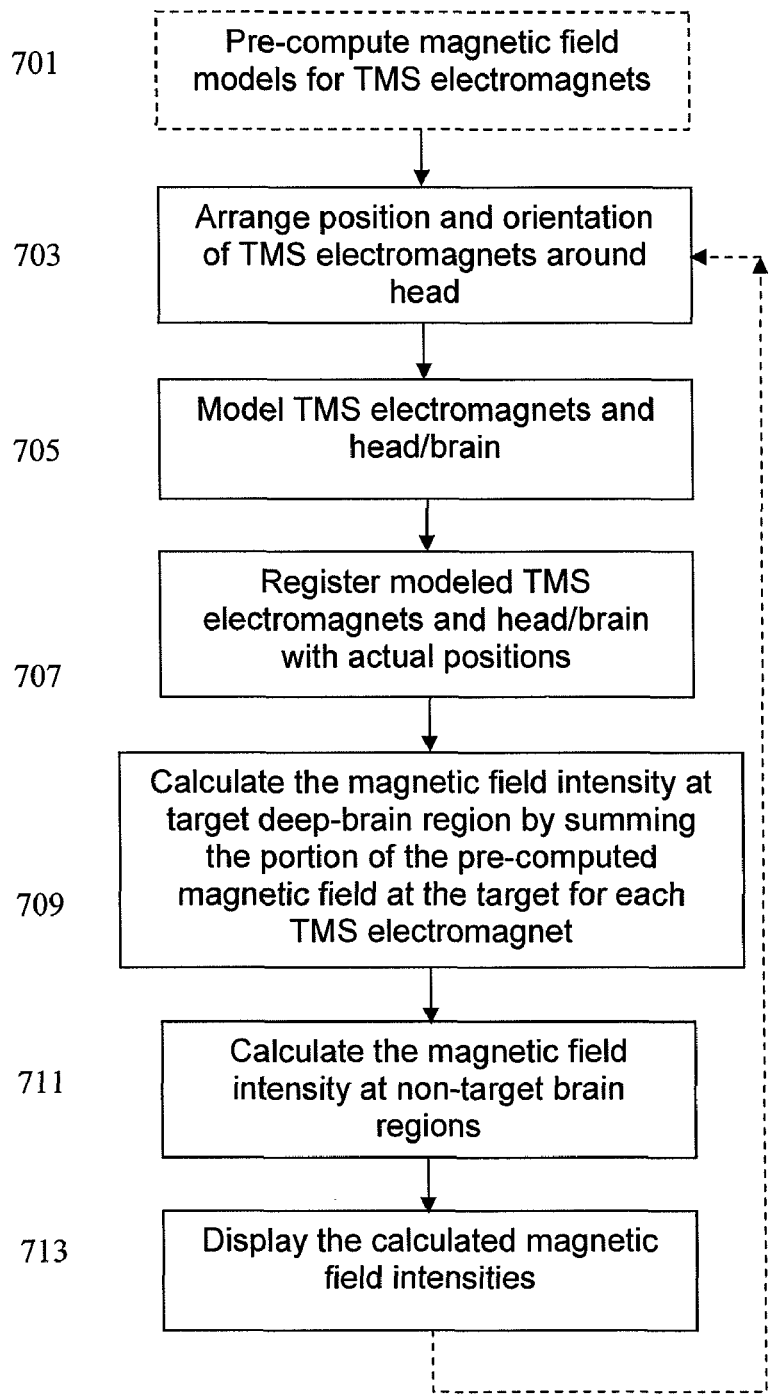
FIG. 7 is a flow chart showing one method of modeling the effect of Transcranial Magnetic Stimulation (TMS) on a deep brain target.
Figure 8:
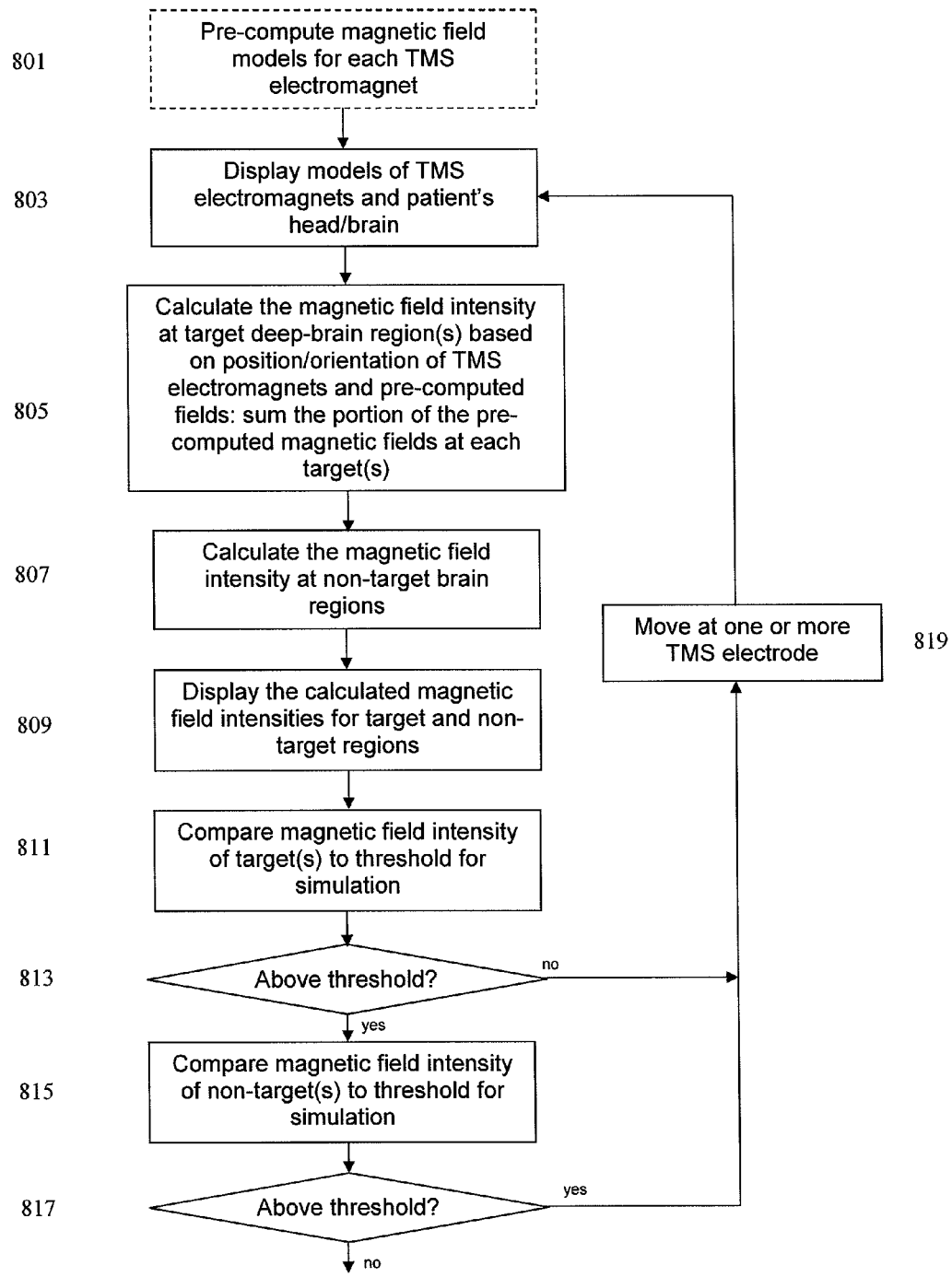
FIG. 8 is a flow chart showing one method of generating a Transcranial Magnetic Stimulation (TMS) treatment plan for a patient.

FIG. 7 is a flowchart showing one method of modeling the effect of Transcranial Magnetic Stimulation (TMS) on a deep brain target, and FIG. 8 is a flowchart showing one method of generating a Transcranial Magnetic Stimulation (TMS) treatment plan for a patient. The details of these methods is as described above, however the flowcharts illustrate one variation of the order in which the steps may occur, including repeating steps. For example, the first (optional) step 701, 801 may be to determine the pre-computed magnetic field model for each of the TMS electromagnets.

Figure 9:
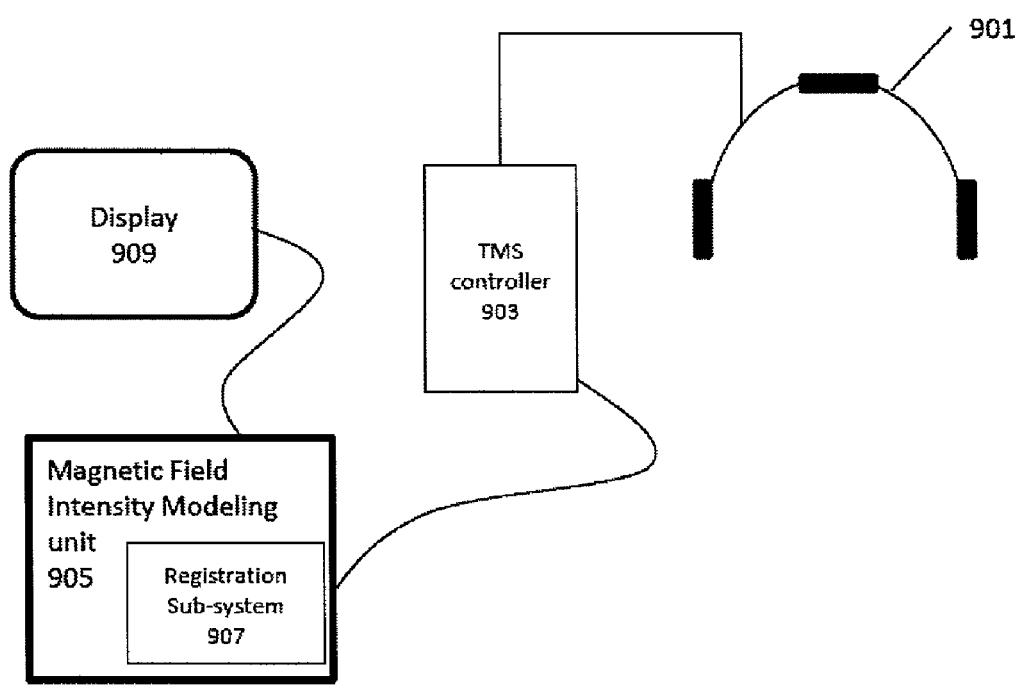
FIG. 9 schematically illustrates one variation of a system for modeling the effect of Transcranial Magnetic Stimulation (TMS) on a deep brain target.

A system, such as the system illustrated schematically in FIG. 9, may be used to model and display the TMS of a deep brain target. Minimally, a system for modeling TMS could include a magnetic field intensity modeling unit 905 and a display 909. The magnetic field intensity modeling unit 905 is configured to model both a patient's head and/or brain, and a plurality of TMS electromagnets, and allow a user to reposition the simulated TMS electromagnets at different positions around the head. As mentioned above, images or a digital representation of a patient's head (e.g., MRI or other brain scans) may be used, and may be input into the magnetic field intensity modeling unit. The modeling unit may include software, hardware and/or firmware configured to output the displays described herein, and to calculate the intensity of the magnetic field at various brain regions (or through the entire brain), including the regions of overlapping magnetic fields due to more than one TMS electromagnet. Thus, the magnetic field intensity modeling unit may also receive input regarding the TMS electromagnets. In particular, the magnetic field intensity modeling unit may receive the pre-calculated magnetic field model for each TMS electromagnet. In some variations the magnetic field intensity modeling unit is configured to receive information on the configuration of one or more TMS electromagnet and pre-calculate the magnetic field model for that TMS electromagnet.

In some variations the system for modeling and displaying magnetic field intensities due to TMS in a patient's brain is configured to arrange the simulated TMS coil representations around the simulation of the patient's head and/or brain based on the actual position of a plurality of TMS coils arranged around the subject's head. Thus, the system may include one or more registration sub-systems 907 for determining the positions and orientations of a plurality of TMS electromagnets 901 positioned around a subject's head. As illustrated in FIG. 9, the system may include a TMS controller 903 for controlling the positions and/or activation of the plurality of TMS electromagnets 901. The TMS controller 903 may also be used to execute a treatment plan that has been identified by the magnetic field intensity modeling unit 905. Thus, a magnetic field intensity modeling unit 905 may store a treatment plan for later execution by the system. A treatment plan may include positions, intensities and/or movement paths for activation of the TMS coils 903. The treatment plan may be displayed 909, so that a user can examine the effect of the treatment plan on one or more target and non-target brain regions, as described above.

While embodiments related to magnetic field strengths are described herein, in some variations the systems and methods described herein may be used to simulate and/or display other parameters, such as profiles of induced electrical currents due to applied magnetic fields.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention, which is set forth in the following claims.

REFERENCES

Avery, D. H., Holtzheimer III, P. E., Fawaz, W., Russo, Joan, Neumaier, J. and Dunner, D. L., Haynor, D. R., Claypoole, K. H., Wajdik, C. and P. Roy-Byrne, "A Controlled Study of Repetitive Transcranial Magnetic Stimulation in Medication-Resistant Major Depression," Biological Psychiatry, 2005; 59:187-194.

Mishelevich, D. J. and M. B. Schneider, U.S. patent application Ser. No. 11/429,504 "Trajectory-Based Transcranial Magnetic Stimulation"

Schneider, M. B. and D. J. Mishelevich, U.S. patent application Ser. No. 10/821,807 "Robotic apparatus for targeting and producing deep, focused transcranial magnetic stimulation"

Hurme, R., I. Autio, P. Sipilia, and J. Ruohonen, U.S. patent application Ser. No. 11/853,232 and International Patent Application PCT/EP2007/059589, "Method and System for Displaying the Electric Field Generated on the Brain by Transcranial Magnetic Stimulation,"

Wagner T. A., Zahn, M., Grodzinsky A. J., Pascual-Leone A., "Three-dimensional head model simulation of transcranial magnetic stimulation," IEEE Trans. Biomed. Eng. 2004 September; 51(9):1586-98.

Davey K., Epstein C. M., George, M. S., and D. E. Bohning, "Modeling the effects of electrical conductivity of the head on the induced electric field in the brain during magnetic stimulation. Clin. Neurophysiol. 2003 November; 114(11):2204-9.

What is claimed is:

1. A method of generating a Transcranial Magnetic Stimulation (TMS) treatment plan for a patient, the method comprising the steps of:
    displaying representations of a plurality of TMS electromagnets around a model of the patient's brain;
    calculating the intensity of the magnetic field for a plurality of brain regions including a deep brain target based on the positions of the TMS electromagnets relative to the brain and based on pre-computed magnetic field models for each of the plurality of TMS electromagnets;
    displaying the magnetic field intensity at the deep brain target on the model of the patient's brain and on non-target regions in the patient's brain; and
    moving the representation of at least one TMS electromagnet and re-calculating the intensity of the magnetic field for the deep brain target until the magnetic field intensity at the deep brain target is above a stimulation threshold while the magnetic field intensity at non-target regions is below a stimulation threshold.

2. The method of claim 1, further comprising displaying a model of the patient's brain and determining a deep brain target on the model of the patient's brain.

3. The method of claim 1, further comprising pre-computing the magnetic field model for each of the TMS electromagnets.

4. The method of claim 1, further comprising registering the position of the representations of the TMS electromagnets relative to the model of the patient's head with the position of actual TMS electromagnets relative to the patient's head.

5. The method of claim 1, wherein the step of calculating the intensity of the magnetic field for each of a plurality of brain regions comprises linearly summing the overlapping magnetic field intensities for each brain region.

6. A method of generating a Transcranial Magnetic Stimulation (TMS) treatment plan for a patient, the method comprising the steps of:
    displaying representations of a plurality of TMS electromagnets around a model of the patient's brain;
    calculating the intensity of the magnetic field for a deep brain target based on the positions of the TMS electromagnets relative to the brain and based on pre-computed magnetic field models for each of the plurality of TMS electromagnets;
    displaying the magnetic field intensity at the deep brain target on the model of the patient's brain; and
    repositioning the representation of at least one TMS electromagnet and re-calculating the intensity of the magnetic field for the deep brain target until the magnetic field intensity at the deep brain target is above a stimulation threshold while the magnetic field intensity at non-target regions is below a stimulation threshold.

7. The method of claim 6, further comprising displaying a model of the patient's brain and determining a deep brain target on the model of the patient's brain.

8. The method of claim 6, further comprising pre-computing the magnetic field model for each of the TMS electromagnets.

9. The method of claim 6, further comprising registering the position of the representations of the TMS electromagnets relative to the model of the patient's head with the position of actual TMS electromagnets relative to the patient's head.

10. The method of claim 6, wherein calculating the intensity of the magnetic field for each of a plurality of brain regions comprises linearly summing the overlapping magnetic field intensities for each brain region.

11. A method of generating a Transcranial Magnetic Stimulation (TMS) treatment plan for a patient, the method comprising the steps of:
    modeling representations of a plurality of TMS electromagnets around a model of the patient's brain;
    calculating the intensity of the magnetic field for a deep brain target based on the positions of the TMS electromagnets relative to the brain and based on pre-computed magnetic field models for each of the plurality of TMS electromagnets;
    displaying the magnetic field intensity at the deep brain target on the model of the patient's brain; and
    repositioning the representation of at least one TMS electromagnet and re-calculating the intensity of the magnetic field for the deep brain target until the magnetic field intensity at the deep brain target is above a stimulation threshold while the magnetic field intensity at non-target regions is below a stimulation threshold.

* * * * *